United States Patent [19]

Mroszczak et al.

[11] 4,397,862
[45] Aug. 9, 1983

[54] GASTROINTESTINAL SPARING THIOESTER DRUGS

[75] Inventors: Edward Mroszczak, Mountain View; Richard Runkel, Palo Alto, both of Calif.

[73] Assignee: Syntex (U.S.A.) Inc., Palo Alto, Calif.

[21] Appl. No.: 310,554

[22] Filed: Oct. 13, 1981

[51] Int. Cl.³ .................... A61K 31/40; C07D 487/04
[52] U.S. Cl. .............................. 424/274; 260/455 R; 424/245; 424/301; 548/403; 548/453; 548/500
[58] Field of Search ................ 548/453, 403; 424/274, 424/245

[56] References Cited
U.S. PATENT DOCUMENTS 4,140,698 2/1979 Van Horn et al. ................. 548/453
4,232,038 11/1980 Kluge et al. ..................... 548/453 X Primary Examiner—Richard Raymond
Attorney, Agent, or Firm—Tom M. Moran; Alan M. Krubiner

[57] ABSTRACT

Compounds of the formula:

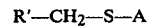

wherein:
R' is hydrogen, alkyl, —COOH or its pharmaceutically acceptable salts, —alkylene—COOH or its pharmaceutically acceptable salts, —alkylene-$SO_2H$ or its pharmaceutically acceptable salts, —alkylene-$SO_3H$ or its pharmaceutically acceptable salts, or —alkylene $CH_2OH$; and
A is the acyl moiety of a pharmaceutically acceptable carboxylic acid, said acid having antiinflammatory properties;
are gastrointestinal tract sparing drugs for antiinflammatory pharmaceuticals.

6 Claims, No Drawings

GASTROINTESTINAL SPARING THIOESTER DRUGS

BACKGROUND OF THE INVENTION

Antiinflammatory drugs are most commonly used for the treatment of such chronic diseases as rheumatism and arthritis. Since such treatment is inherently on a long-term basis, irritating side effects caused by such drugs may be accentuated due simply to the long-term dosage which must be administered. Further, many antiinflammatory drugs contain carboxylic acid groups, which are in close proximity to an aryl substituent; such a configuration in the structure of the drug is thought to inhibit the release of those prostaglandins which are responsible for the maintenance of a healthy intestinal mucosa. Accordingly, many antiinflammatory drugs are associated with gastrointestinal irritation leading to abdominal pain, exacerbation of any existing ulcerous condition and possibly even creation of an ulcerous condition.

It is known that esterified acyl groups fail to exhibit this deleterious effect if the ester is not hydrolyzed in the gastrointestinal tract, but is hydrolyzed after being absorbed into the bloodstream. See, for example, Arzneimeittel Forschung, 8a/1980: 1424, which discloses that acemetacin, an oxy ester, is relatively non-irritating in the gastrointestinal tract in comparison with the corresponding free acid indomethacin. Also, see U.S. Pat. No. 3,988,446 which discloses glycerides esterified to antiinflammatory acids, to achieve a similar effect.

The present invention utilizes thioester derivatives thus utilizing their stability in the acidic conditions of the stomach. As they are absorbed into the bloodstream, and as such hydrolysis occurs there, the antiinflammatory effect then arises without the gastrointestinal irritation.

(The compounds may also be applied topically. Of course, in this case, gastrointestinal irritation is not relevant; but the compounds of the invention are here advantageous in that they are more expeditiously absorbed by the subject than the unesterified drug.)

SUMMARY OF THE INVENTION

The invention herein concerns thioesters of the formula:

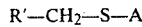

wherein:

R′ is hydrogen, alkyl, —COOH or its pharmaceutically acceptable salts, -alkylene-COOH or its pharmaceutically acceptable salts, —alkylene-SO$_2$H or its pharmaceutically acceptable salts, —alkylene-SO$_3$H or its pharmaceutically acceptable salts, or -alkylene CH$_2$OH; and A is the acyl moiety of a pharmaceutically acceptable carboxylic acid, said acid having antiinflammatory properties.

In another aspect the invention concerns methods of inhibiting or treating inflammation in human beings, and compositions therefor, which employ the thioesters described above.

DETAILED DESCRIPTION OF THE INVENTION

Definitions:

As used herein:

"Alkyl" means a branched or unbranched saturated hydrocarbon chain containing 1-6 carbon atoms, such as methyl, ethyl, propyl, tert-butyl, n-hexyl and the like;

"Lower alkyl" means a branched or unbranched saturated hydrocarbon chain of 1-4 carbons, such as, for example, methyl, ethyl, n-propyl, i-butyl and the like.

"Alkoxy" means the group —OR wherein R is alkyl as herein defined.

"Alkylene" means a branched or unbranched saturated hydrocarbon diradical of 1-6 carbons, such as, for example

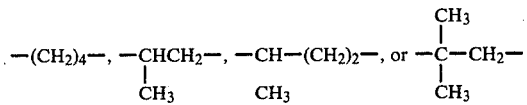

"Acyl moiety of a pharmaceutically acceptable carboxylic acid, said acid having anti-inflammatory properties." means, for example, the acyl moieties of those carboxylic acids disclosed in U.S. Pat. Nos. 4,089,969, 4,087,539, 4,097,579, 4,344,943, indomethacin, aspirin, or naproxen.

"Pharmaceutically acceptable salts" means salts derived from pharmaceutically acceptable, non-toxic inorganic and organic bases. Salts derived from inorganic bases include sodium, potassium, lithium, ammonium, calcium, magnesium, ferrous, zinc, copper, manganous, aluminum, ferric, maganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

Preparation Methods:

The compounds are prepared by conventional esterification of the antiinflammatory acid with a mercaptan of the formula R′—CH$_2$—SH wherein R′ is as herein defined. Methods for such esterifications are well known to those in the art.

In general, an activated derivative of the carboxylic acid is treated, preferably in the presence of base, with the mercaptan or with a sodium salt or other salt thereof. The acid is preferably first activated with, for example, thionyl chloride or diphenylchlorophosphate to form the corresponding acyl halide or anhydride. Specifically, the carboxylic acid is dissolved in an inert organic solvent such as, for instance, tetrahydrofuran, ether, or dimethylformamide, preferably tetrahydrofuran. A small quantity (preferably of approximately equimolar amount) of an appropriate base, such as pyridine or triethylamine is optionally added. The mixture may not be in true solution; the temperature is between about 0° to 100°, preferably around 45° to 60°. An "activating agent" such as, for example, thionyl chloride or diphenylchlorophosphate is then added in approximately equimolar amount to the carboxylic acid. The mixture is allowed to react for about ten minutes to about twenty-four hours, preferably about 1 to 2 hours, and then cooled in an ice bath. During the entire procedure, the mixture is kept under an inert atmosphere, such as argon or nitrogen.

Following the activation of the acid, a slight molar excess of the mercaptan or of the corresponding metal salt, preferably the sodium salt, is then added to the solution of the activated carboxylic acid and the mixture is kept at about 20° to about 100°, preferably 45° to 60° until the reaction is complete, roughly 1 to 3 hours.

(Alternatively, the activated carboxylic acid may be isolated, for example by evaporation of the solvent(s), before being reacted with the mercaptan or a metal salt thereof, in a suitable organic solvent.) The product is then isolated by conventional means. Such conventional means include, for example, filtration, extraction, crystallization, column chromatography, thin layer chromatography or a combination of the above.

In some embodiments, the antiinflammatory acyl moiety contains a chiral center. Accordingly, the compounds of the present invention may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

If desired, the antiinflammatory acids used herein may be resolved into their optical antipodes by conventional resolution means; for example by separation (e.g. fractional crystallization) of the diastereomeric salts, amines or esters formed by the reaction of these compounds with optically active amines or alcohols. Exemplary of such optically active reagents are the optically active forms of 2-butanol, 2-pentanol, 3-methyl cyclohexanol and the corresponding amines. (Depending on reaction conditions, either salts or amides may be formed by reaction with the amines.) The separated pure diastereomeric esters, amides, or salts may then be cleaved by standard means to afford the respective optical isomers of the antiinflammatory acids from which the thio ester will then be made.

UTILITY AND ADMINISTRATION

The compounds of the invention are gastrointestinal sparing in relation to the amounts required to exert an antiinflammatory effect. Accordingly, the compounds of the invention are directed to oral administration and are particularly useful when administered orally.

For said oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, and the like, and may contain 1%-95% active ingredient, preferably 1-70%. Actual methods of preparing such oral dosages are known, or will be apparent, to those skilled in the art; for example, see *Remington's Pharmaceutical Sciences*, Mack Publishing Co., Easton, Pa., 15th edition, 1975.

The dosage administered will, of course, depend on the particular antiinflammatory acyl group which is selected, as well as the usual parameters relating to the status of the subject and the judgement of the practitioner. The dosages will vary with the effectiveness of the particular antiinflammatory acid. However, for the ordinary antiinflammatories in the pyrrolopyrrole class, (see, for example, U.S. Pat. No. 4,087,539), an effective dosage would be in the range of approximately 0.1 to 10 mg/kg/day, preferably 0.5 to 1 mg/kg/day.

For topical administration, similar dosage ranges apply. However, the formulation is preferably in the form of a cream or gel. Typical excipients for such preparations include oils, surfactants and hydrophilic polymers; concentrations of active ingredient are preferably in the range of 0.1 to 10%.

PREFERRED EMBODIMENTS

Preferred embodiments of the present invention are those wherein the acyl moiety of the antiinflammatory acid is selected from the group consisting of compounds of the formula:

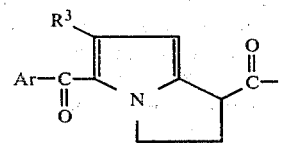

wherein
R³ is hydrogen, halo, or lower alkyl; and Ar is selected from the group consisting of:

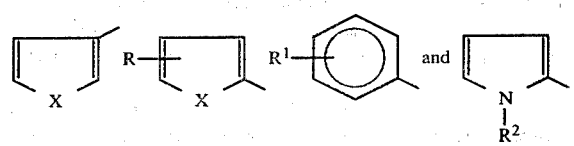

in which
X is O or S;
R is hydrogen, methyl, chloro or bromo;
R¹ is hydrogen, a lower alkyl group having 1 to 4 carbon atoms; a lower alkoxy group having from 1 to 4 carbon atoms, chloro, fluoro or bromo; and
R² is hydrogen or a lower alkyl group having from 1 to 4 carbon atoms.

Again, referencing the formula R'-CH₂-S-A, another set of preferred embodiments is that wherein R' is hydrogen; another that wherein R' is COOH (or its salts).

Particularly preferred are those embodiments wherein R' is either hydrogen or COOH, and wherein the acyl group from the antiinflammatory acid is selected from among those designated as preferred hereinabove.

The following examples serve to illustrate the invention. They should not be construed as narrowing it, or limiting its scope.

EXAMPLE 1

Preparation of methyl 5-benzoyl-1,2-dihydro-3H-pyrrolo[1,2-a]pyrrole-1-thiocarboxylate In a heat-dried, stirred, N₂ blanketed 25 ml flask with side-arm and septum 130 mg of 5-benzoyl-1,2-dihydro- 3H-pyrrolo-[1,2-a]pyrrole-1-carboxylic acid is dissolved in 8 ml of dry THF. Fifty-nine (59) µl of triethylamine, followed by 81 µl of diphenylchlorophosphate are added, and the turbid mixture is heated in a 55° oil bath. After 2 hours the reaction mixture is cooled in ice, and then filtered into a fresh, dry $N_2$ blanketed 50 ml flask with side-arm and septum, washing the filter cake with additional THF.

1.35 ml of a 0.92 N solution of sodium thiomethylate (sodium methyl mercaptan) is added to the solution of the above intermediate in the flask, and the mixture is heated at 55° for 1½ hours, after which the reaction is complete. The resulting product is added to ethyl acetate and dilute aqueous sodium bicarbonate is added. The extract is washed three times with $H_2O$, dried over $Na_2SO_4$, and evaporated to dryness. Two crystallizations of the residue from acetone-hexane affords pure colorless needles of methyl 5-benzoyl-1,2-dihydro-3H-pyrrolo[1,2-a]pyrrole-1-thiocarboxylate, m.p. 69°.

EXAMPLE 2

Preparation of Carboxymethyl Benzoyl-1,2-dihydro-3H-pyrrolo[1,2-a]pyrrole-1-thiocarboxylate To a suspension of 1.0 g of 5-benzoyl-1,2-dihydro-3H-pyrrolo[1,2-a]pyrrole-1-carboxylic acid in 30 ml of dry benzene was added 0.29 ml of thionyl chloride and 0.03 ml of dimethylformamide. The mixture was left for 18 hours at room temperature and then evaporated under vacuum. To the residue so obtained were added 30 ml of ether, 1 ml of thioglycolic acid, and 1 ml of triethylamine. After 24 hours at room temperature, the reaction mixture was added to ethyl acetate, and the resultant solutions was washed with water, dried and evaporated. The residue so obtained was chromatographed on silica gel, eluting with 100:100:2 hexane:ethyl acetate:acetic acid, so as to obtain the desired product as a gum. This material was dissolved in 25 ml of ethyl acetate, and to the resulting solution was added a solution of 1.5 molar equivalents of sodium 2-ethylhexanoate in 20 ml of ethyl acetate. The sodium salt of the desired product precipitated out and was filtered, washed with ethyl acetate and dried under vacuum. The product has a decomposition point of 170°–180° C.

EXAMPLE 3

Similarly, using the procedure outlined in Example 1 or 2, the following compounds of the invention are prepared:
carboxymethyl 5-benzoyl-1,2-dihydro-3H-pyrrolo[1,2-a]pyrrole-1-thiocarboxylate, dec. 170°–180° as the sodium salt;
2-carboxyethyl 5-benzoyl-1,2-dihydro-3H-pyrrolo[1,2-a]pyrrole-1-thiocarboxylate;
3-hydroxypropyl 5-benzoyl-1,2-dihydro-3H-pyrrolo[1,2-a]pyrrole-1-thiocarboxylate;
methyl 5-(4-methoxybenzoyl)-1,2-dihydro-3H-pyrrolo[1,2-a]pyrrole-1-thiocarboxylate;
n-propyl 5-(3,4,-dimethylbenzoyl)-1,2-dihydro-3H-pyrrolo[1,2-a]pyrrole-1-thiocarboxylate;
i-butyl 5-(2-thenoyl)-1,2-dihydro-3H-pyrrolo[1,2-a]pyrrole-1-thiocarboxylate;
4-hydroxybutyl 5-(2-pyrrolyl)-1,2-dihydro-3H-pyrrolo[1,2-a]pyrrole-1-thiocarboxylate;
ethyl 5-(2,6-dichlorobenzoyl)-1,2-dihydro-3H-pyrrolo[1,2-a]pyrrole-1-thiocarboxylate.

The above set of compounds is, of course, merely representative, and should not be construed as exhaustive or limiting. All of the compounds encompassed by the invention may be prepared as set forth hereinabove.

In Examples 4 through 8, the active ingredient is methyl 5-benzoyl-1,2-dihydro-3H-pyrrolo[1,2-a]pyrrolethiocarboxylate. Other compounds of Formula I and the pharmaceutically acceptable salts thereof may be substituted therein.

EXAMPLE 4

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 5

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 6

| Ingredients | Quantity per tablet, mgs. |
|---|---|
| Active ingredient | 200 |
| cornstarch | 50 |
| lactose | 145 |
| magnesium stearate | 5 |

The above ingredients are mixed intimately and pressed into single scored tablets.

EXAMPLE 7

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 8

| Ingredients | Quantity per tablet, mgs. |
|---|---|
| Active ingredient | 150 |
| lactose | 92 |

The above ingredients are mixed and introduced into a hard-shell gelatin capsule.

EXAMPLE 9

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water qs | 100 |

All of the above ingredients, except water, are combined and heated to 60° C. with stirring. A sufficient quantity of water at 60° C. is then added with vigorous stirring to emulsify the ingredients, and water then added q.s. 100 g.

We claim:

1. A compound of the formula:

R'—CH₂—S—A wherein

R' is hydrogen, alkyl, -COOH or its pharmaceutically acceptable salts, —alkylene-COOH or its pharmaceutically acceptable salts, —alkylene-SO₂H or its pharmaceutically acceptable salts, —alkylene-SO₃H or its pharmaceutically acceptable salts, or —alkylene-CH₂OH; and A is the acyl moiety of a pharmaceutically acceptable carboxcylic acid of the formula:

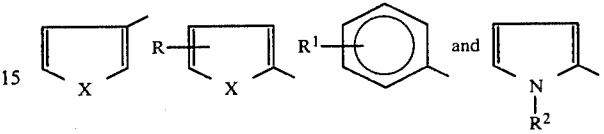

wherein R³ is hydrogen, halo, or lower alkyl; and Ar is selected from the group consisting of:

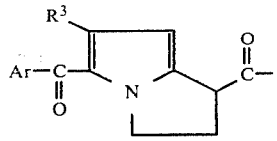

in which X is O or S;

R is hydrogen, methyl, chloro or bromo;

R¹ is hydrogen, a lower alkyl group having 1 to 4 carbon atoms; a lower alkoxy group having from 1 to 4 carbon atoms, chloro, fluoro or bromo; and R² is hydrogen or a lower alkyl group having from 1 to 4 carbon atoms.

2. The compound of claim 1 wherein R' is hydrogen.

3. The compound of claim 1 wherein R' is —COOH, or its pharmaceutically acceptable salts.

4. The compound of claim 3 wherein
   Ar is phenyl;
   R¹ is hydrogen; and
   R³ is hydrogen,
namely carboxymethyl benzoyl-1,2-dihydro-3H-pyrrolo[1,2-a]pyrrole-1-thiocarboxylate.

5. A pharmaceutical composition for inhibiting inflammation in human beings which comprises a therapeutically effective amount of a compound of claim 1 or a pharmaceutically acceptable acid addition salt thereof in admixture with a pharmaceutically acceptable excipient.

6. A method for inhibiting inflammation in human beings which method comprises administering to a subject in need of such treatment a therapeutically effective amount of, or a pharmaceutical composition containing a therapeutically effective amount of, the compound of claim 1 or a pharmaceutically acceptable acid addition salt thereof.

* * * * *